United States Patent
Xu et al.

(10) Patent No.: US 11,497,504 B2
(45) Date of Patent: Nov. 15, 2022

(54) ANEURYSM TREATMENT WITH PUSHABLE IMPLANTED BRAID

(71) Applicant: DePuy Synthes Products, Inc., Raynham, MA (US)

(72) Inventors: Ruijiao Xu, Miami Lakes, FL (US); Lacey Gorochow, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 176 days.

(21) Appl. No.: 16/853,135

(22) Filed: Apr. 20, 2020

(65) Prior Publication Data
US 2020/0367899 A1    Nov. 26, 2020

Related U.S. Application Data

(63) Continuation-in-part of application No. 16/418,199, filed on May 21, 2019, now Pat. No. 10,653,425.

(51) Int. Cl.
*A61B 17/12* (2006.01)

(52) U.S. Cl.
CPC .. *A61B 17/12113* (2013.01); *A61B 17/12145* (2013.01)

(58) Field of Classification Search
CPC ........ A61B 17/12022; A61B 17/12031; A61B 17/12109; A61B 17/12113; A61B 17/1214; A61B 17/12145; A61B 17/12168; A61B 17/12172
See application file for complete search history.

(56) References Cited

U.S. PATENT DOCUMENTS

| | | | |
|---|---|---|---|
| 2,849,002 | A | 8/1958 | Oddo |
| 3,480,017 | A | 11/1969 | Shute |
| 4,085,757 | A | 4/1978 | Pevsner |
| 4,282,875 | A | 4/1981 | Serbinenko et al. |

(Continued)

FOREIGN PATENT DOCUMENTS

| | | |
|---|---|---|
| CA | 2395796 A1 | 7/2001 |
| CA | 2 431 594 A1 | 9/2002 |

(Continued)

OTHER PUBLICATIONS

Extended European Search Report issued in corresponding European Patent Application No. 20 21 2968 dated May 11, 2021.

(Continued)

*Primary Examiner* — Todd J Scherbel
(74) *Attorney, Agent, or Firm* — Troutman Pepper Hamilton Sanders LLP

(57) ABSTRACT

The present invention provides a braided implant with a retractable dual proximal layer and methods for administering the braided implant to treat aneurysms. The implant can include a tubular braid that can be set into a predetermined shape, compressed for delivery through a microcatheter, and implanted in at least one implanted position that is based on the predetermined shape and the geometry of the aneurysm in which the braid is implanted. The implant can also have a retractable dual layer at the proximal end of the device made of the same braid to provide additional coverage at the neck of the aneurysm. The dual layer can be pressed distally into a first implanted portion of the tubular braid, moving the first portion of the tubular braid towards the distal portion of an aneurysm wall so that the implant can partially or completely occlude an aneurysm neck.

9 Claims, 8 Drawing Sheets

(56) References Cited

U.S. PATENT DOCUMENTS

| | | |
|---|---|---|
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Gia et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi et al. |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 3,048,145 A1 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | Van Der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,974,512 B2 | 3/2015 | Aboytes et al. |
| 8,992,568 B2 | 3/2015 | Duggal et al. |
| 8,998,947 B2 | 4/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |

(56) References Cited

U.S. PATENT DOCUMENTS

| | | |
|---|---|---|
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy et al. |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace et al. |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0277013 A1 | 9/2014 | Sepetka et al. |

(56) References Cited

U.S. PATENT DOCUMENTS

| | | |
|---|---|---|
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0206850 A1 | 7/2018 | Wang et al. |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow |
| 2020/0000477 A1 | 1/2020 | Nita et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |

(56) References Cited

FOREIGN PATENT DOCUMENTS

| | | |
|---|---|---|
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2016 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | 2005/117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | 2015/160721 A1 | 10/2015 |
| WO | 2015/171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2019/038293 A1 | 2/2019 |
| WO | WO 2012/034135 A1 | 3/2021 |

OTHER PUBLICATIONS

Altes et al., Creation of Saccular Aneurysms in the Rabbit: A Model Suitable for Testing Endovascular Devices AJR 2000; 174: 349-354.
Schaffer, Advanced Materials & Processes, Oct. 2002, pp. 51-54.
Extended European Search Report issued in corresponding European Patent Application No. 19 21 5277 dated May 12, 2020.
File History for corresponding U.S. Appl. No. 15/430,141, filed Feb. 10, 2017 cited by Applicant in parent U.S. Appl. No. 16/418,199.
File History for corresponding U.S. Appl. No. 15/430,419, filed Feb. 10, 2017 cited by Applicant in parent U.S. Appl. No. 16/418,199.
File History for corresponding U.S. Appl. No. 62/293,710, filed Feb. 10, 2017 cited by Applicant in parent U.S. Appl. No. 16/418,199.

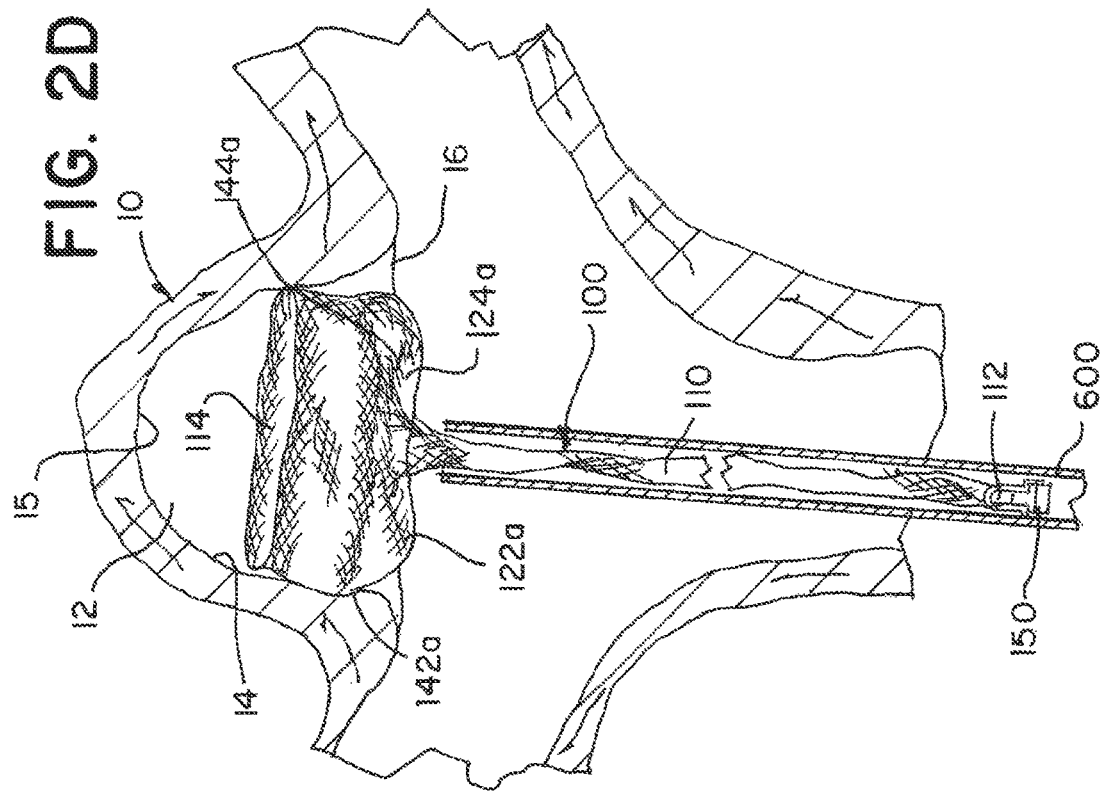
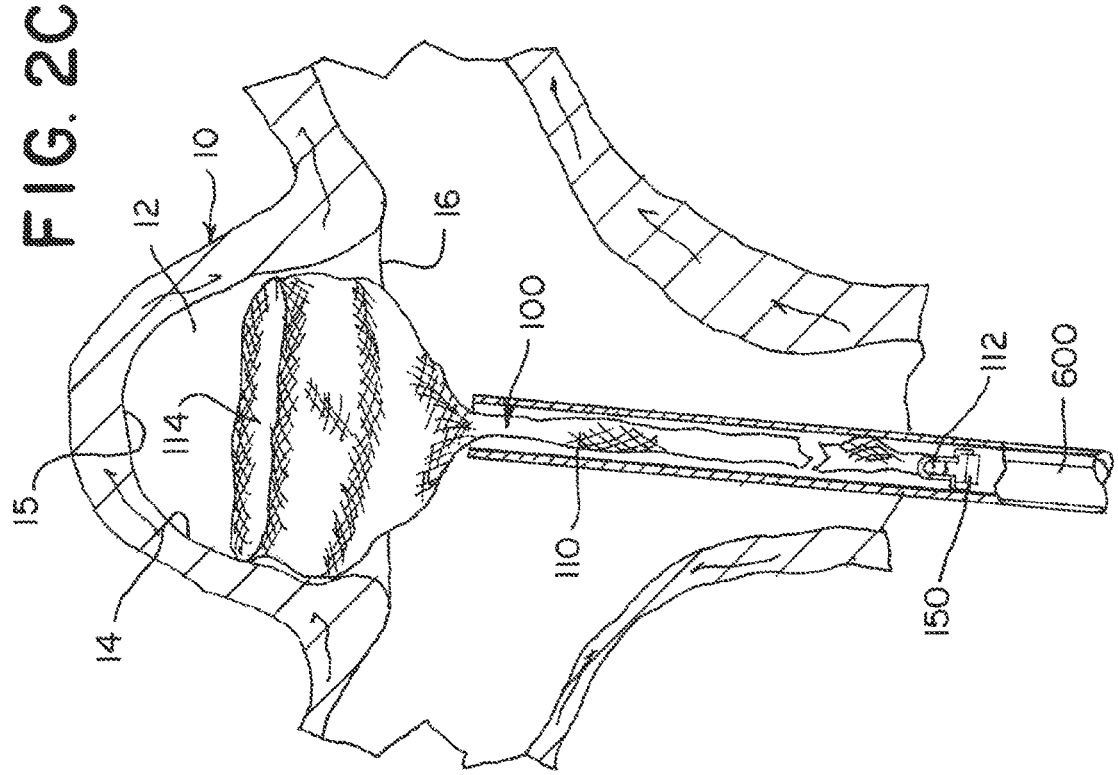

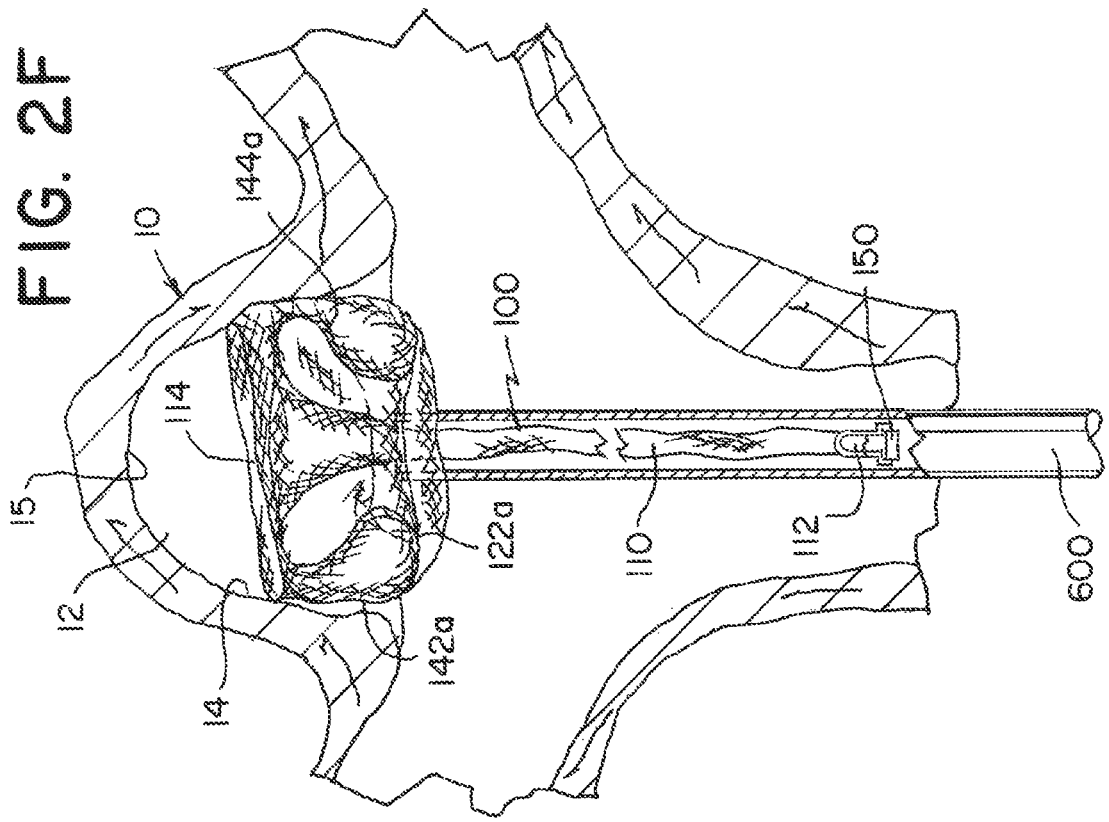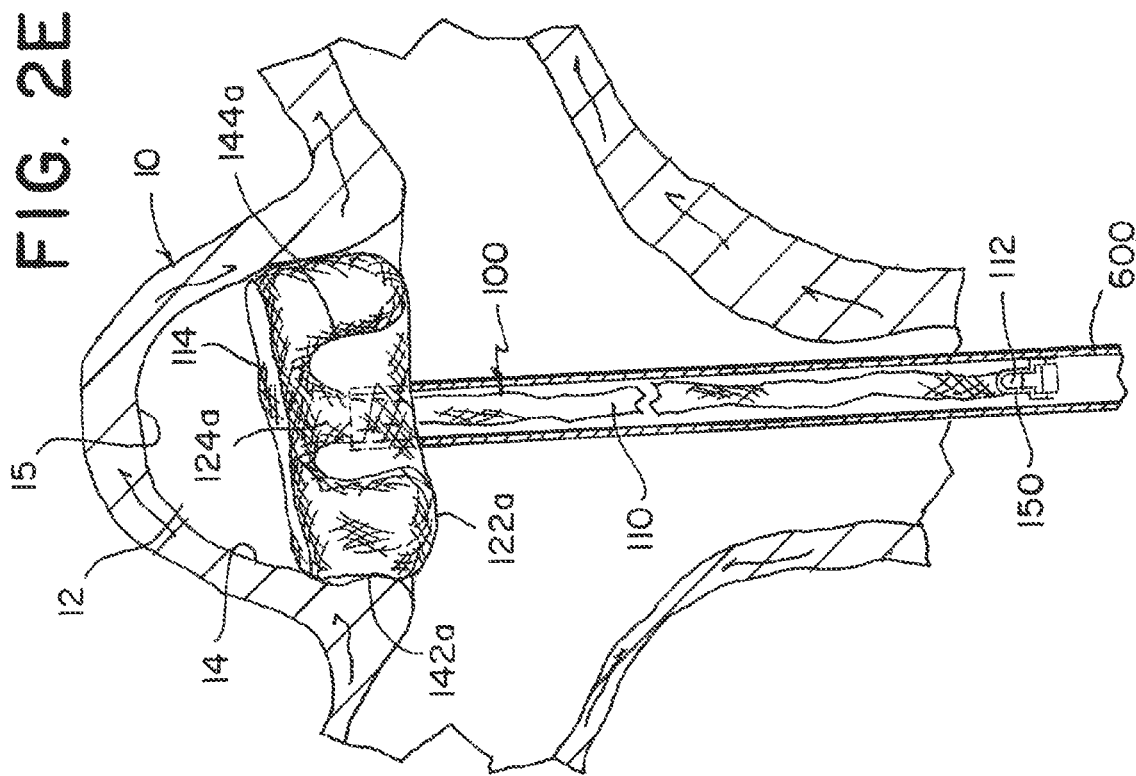

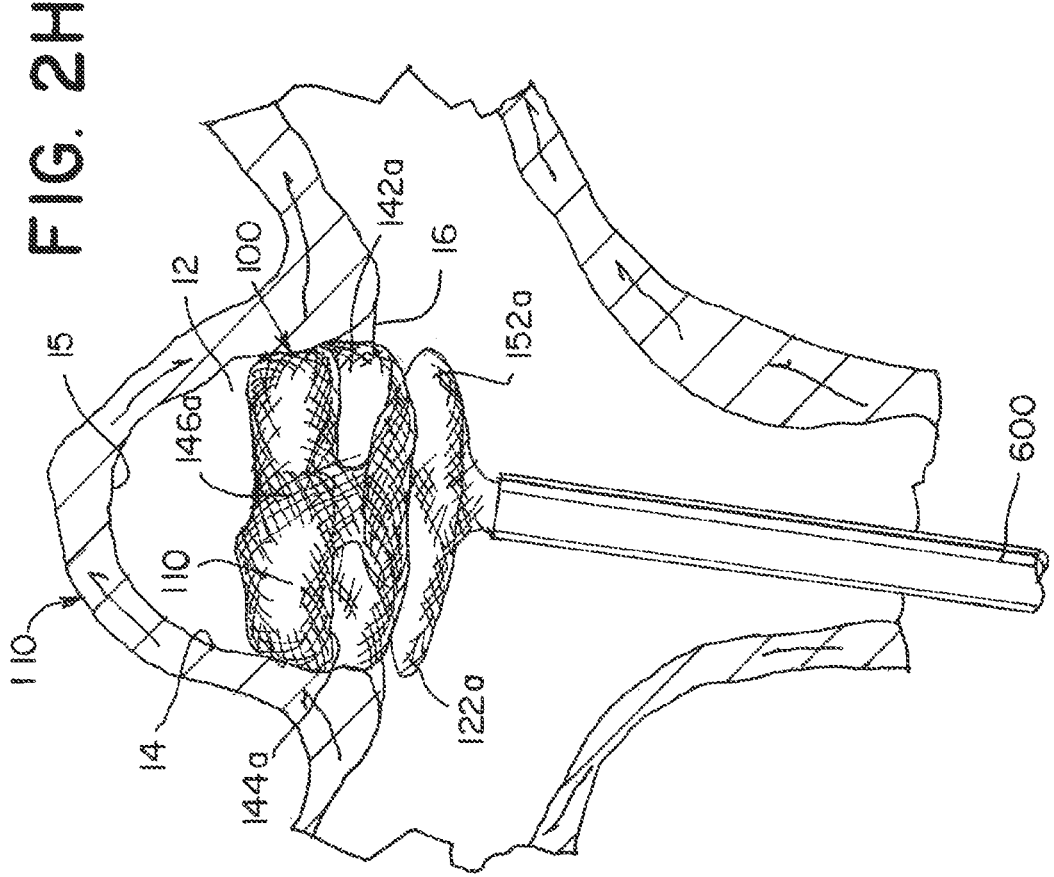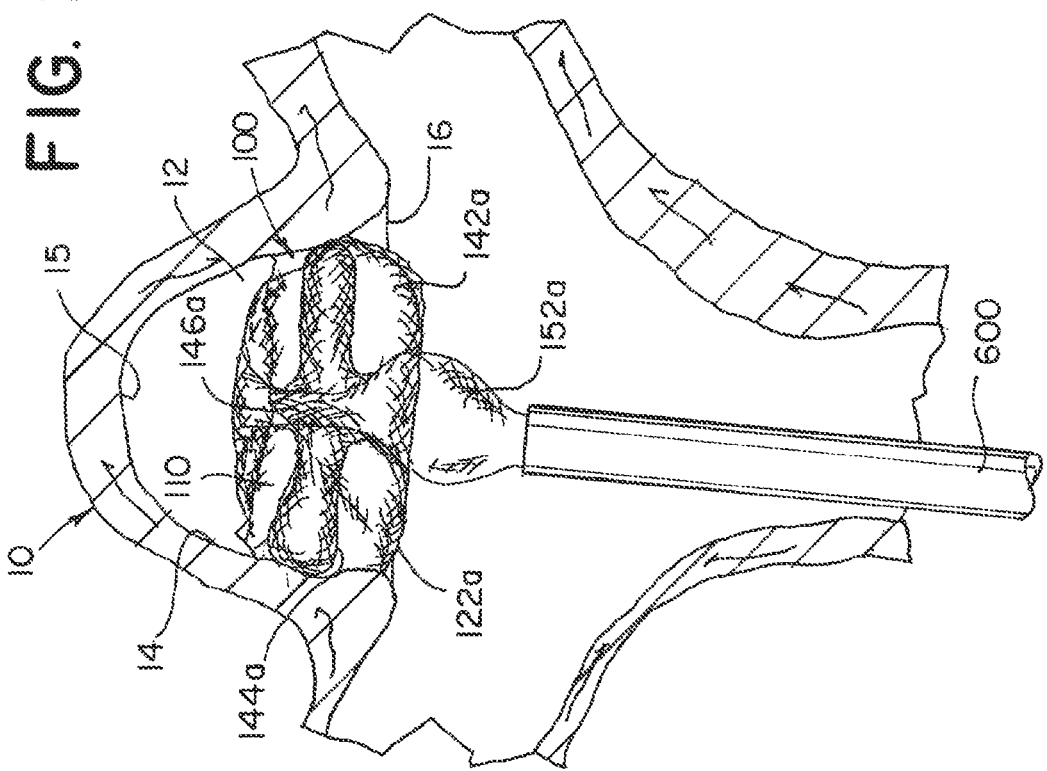

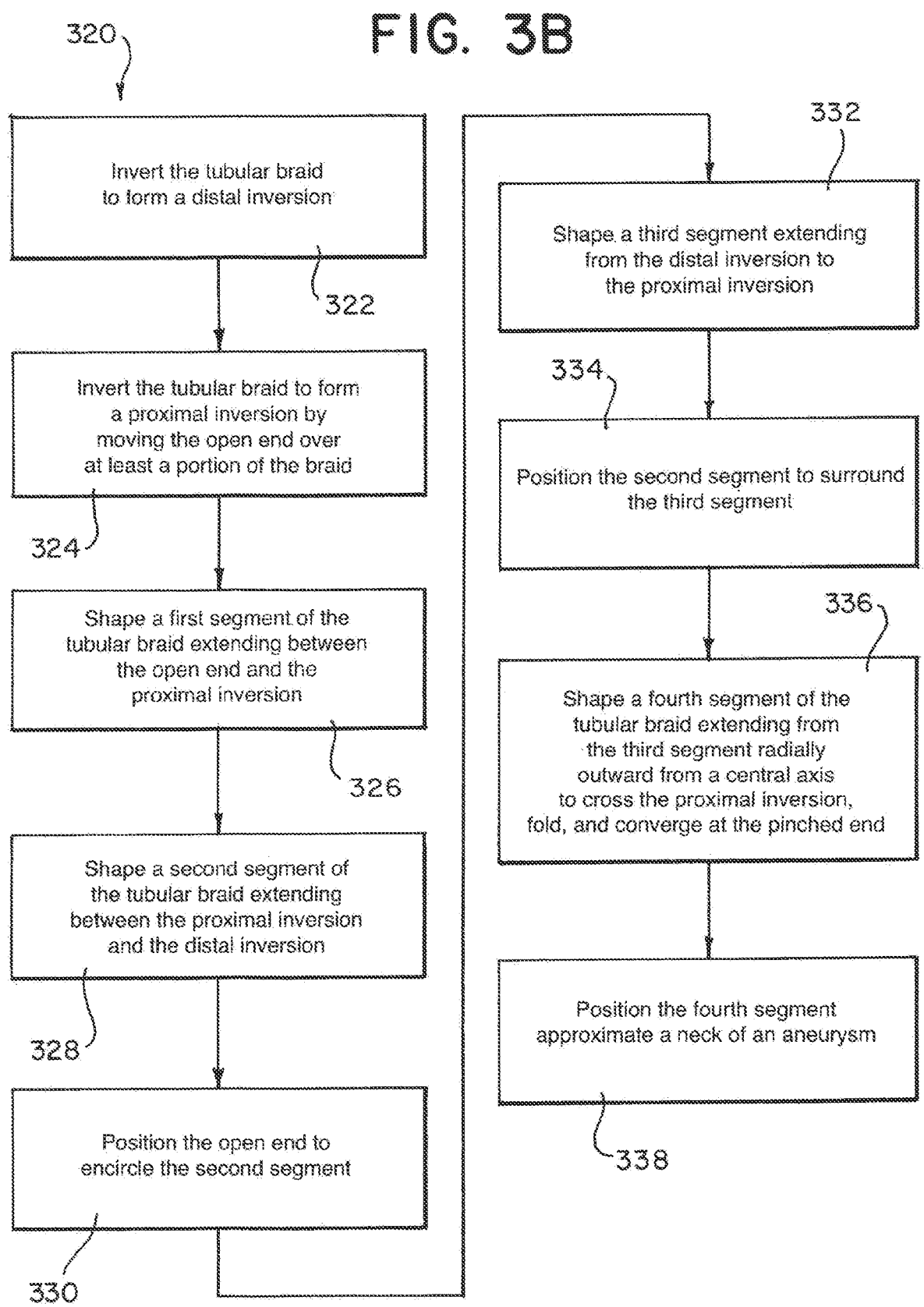

ANEURYSM TREATMENT WITH PUSHABLE IMPLANTED BRAID

CROSS-REFERENCE TO RELATED APPLICATIONS

This application is a Continuation-In-Part to U.S. application Ser. No. 16/418,199 filed May 21, 2019, and this application in incorporated herein in its entirety.

FIELD OF THE INVENTION

The present invention generally relates to medical instruments, and more particularly, to embolic implants for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the brain tissue surrounding cranial vessels and the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves.

For example, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Another particular type of occlusive approach endeavors to deliver and treat the entrance or "neck" of the aneurysm. In such "neck" approaches, by minimizing blood flow across the neck, a cessation of flow into the aneurysm may be achieved. It is understood that the neck plane is an imaginary surface where the inner most layer of the parent wall would be but for the aneurysm. However, neck-occlusive approaches, such as implanting a flow impeding device in the parent vessel, are not without drawbacks. Such an approach may impede blood flow into peripheral blood vessels while blocking the aneurysm neck in the parent vessel. Impeding flow to the peripheral blood vessel can unintentionally lead to severe damage if the openings of the vessels are blocked.

Alternatives to embolic coils are being explored, such as tubular braided implants. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants. For instance, delivery of tubular braided implants can require unique delivery systems to prevent the braid from inverting or abrading when pushed through a microcatheter, and some simple delivery systems that push embolic coils through microcatheters from their proximal end may not be effective to deliver tubular braids.

There is therefore a need for improved methods, devices, and systems for implants for aneurysm treatment.

SUMMARY

It is an object of the present invention to provide systems, devices, and methods to meet the above-stated needs. Generally, it is an object of the present invention to provide a braided implant with a retractable dual proximal layer. The implant can secure within an aneurysm sac and occlude at least a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted. The implant can also have a retractable dual layer at the proximal end of the device made of the same braid to provide additional coverage at the neck of the aneurysm.

In some examples presented herein, the dual layer can be shaped by expanding it radially, and the dual layer can be pressed distally into a first portion of the tubular braid already within the aneurysm. By pressing the dual layer distally into the first portion of the tubular braid, the first portion of the tubular braid can be moved towards the distal portion of an aneurysm wall so that the implant can partially or completely occlude an aneurysm neck. Pushing the dual layer into the first portion of the braid can help conform the implant to the shape of the aneurysm and resist compaction. The dual layer when expanded radially and pressed into the first portion of the braid also can provide additional coverage at the neck of the aneurysm to increase thrombosis. In some examples, the dual layer can also be placed within the aneurysm sac with only a detachment point external to the sac.

In some examples, the tubular braid can include memory shape material that can be heat set to a predetermined shape, can be deformed for delivery through a catheter, and can self-expand to an implanted shape that is based on the predetermined shape and confined by the anatomy of the aneurysm in which it is implanted.

In some examples the tubular braid can be shaped to a delivery shape that is extended to a single layer of tubular braid having a compressed circumference/diameter sized to be delivered through the microcatheter.

In some examples, before the implant is released from the delivery system, the implant can be partially or fully retracted into the microcatheter and repositioned.

An example method for forming an occlusive device to treat an aneurysm can include one or more of the following steps presented in no particular order, and the method can include additional steps not included here. An implant with a tubular braid, an open end, and a pinched end can be selected. The tubular braid can be shaped to a predetermined shape. Shaping the tubular braid to a predetermined shape can also include further steps. These steps can include inverting the tubular braid to form a distal inversion. The tubular braid can also be inverted to form a proximal inversion by moving the open end over at least a portion of the braid. A first segment of the tubular braid extending between the open end and the proximal inversion can be shaped. A second segment of the tubular braid extending between the proximal inversion and the distal inversion can be shaped. The open end can be positioned to encircle the second segment. A third segment extending from the distal inversion to the proximal inversion can be shaped. The second segment can be positioned to surround the third segment. A fourth segment of the tubular braid extending from the third segment radially outward from a central axis to cross the proximal inversion can be shaped and can fold and converge at the pinched end. The fourth segment can be positioned near the neck of an aneurysm.

An example method for treating an aneurysm can include one or more of the following steps presented in no particular order, and the method can include additional steps not included here. A first portion of a tubular braided implant, which can have a tubular braid, an open end, and a pinched end, can be positioned within a sac of the aneurysm such that the first portion circumferentially apposes walls within the sac. The first portion can have one or more inversions. A second portion of the tubular braided implant can be expanded radially to occlude a majority of a neck of the aneurysm. The second portion can be pressed distally into the first portion. The first portion of the tubular braided implant can be moved toward a distal portion of the aneurysm wall as a result of pressing the second portion distally into the first portion.

In some examples, expanding the second portion of the tubular braided implant can include positioning a fold in the second segment to define a substantially circular perimeter of the second portion and compressing the second portion along a central axis of the tubular braided implant such that the second portion can have a substantially circular shape having an area and two layers of braid over a majority of the area of the substantially circular shape.

In some examples, positioning the first portion of the tubular braided implant can further include shaping the tubular braided implant to form a columnar post encircling a central axis of the tubular braided implant and extending a majority of a height of the first portion. In another example, positioning the first portion of the tubular braided implant can further involve positioning a proximal inversion near the neck of the aneurysm and positioning a distal inversion approximate the distal portion of the aneurysm wall. In another example, positioning the first portion of the tubular braided implant can further involve positioning the open end of the tubular braided implant to circumferentially appose the aneurysm wall, shaping a first segment of the tubular braid extending between the open end and the proximal inversion to appose at least a portion of a wall of the aneurysm within the aneurysm's sac, and shaping a second segment of the tubular braid such that the first segment provides an outwardly radial force in a plane defining a boundary between the aneurysm and blood vessel branches, the force sufficient to appose the first segment to walls of the aneurysm.

In some examples, pressing the second portion distally into the first portion can further involve pressing the second portion of the tubular braided implant against the proximal inversion in the first portion of the tubular braided implant.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 2A through 2I are illustrations of an implant having a tubular braid that expands to an implanted shape similar to as illustrated in FIG. 1B as the tubular braid exits a microcatheter according to aspects of the present inventions;

FIGS. 3A through 3B are flow diagrams for a method of forming an occlusive device to treat an aneurysm.

DETAILED DESCRIPTION

Examples presented herein generally include a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted. The implant can include a single layer of braid (e.g. a braid that can be extended to form a single layer tube) heat treated into multiple layers with retractable dual layer at the proximal end of the tubular braid. When compressed, the implant can be sufficiently short to mitigate friction forces produced when the implant is delivered unsheathed through the microcatheter.

A first portion of the tubular braid can be positioned in an aneurysm, after which the retractable dual layer can be deployed from the microcatheter and pushed onto the first portion of the tubular braid. This configuration provides three layers of braid at the neck of the aneurysm. The dual layer can potentially cover any gap between the first portion of implanted tubular braid and the aneurysm neck, and can potentially increase metal coverage, decrease porosity of the implant, and increase stasis and blood flow diversion at the neck of the aneurysm to promote the sealing and healing of the aneurysm compared a similarly shaped braided implant lacking the dual layer. The entire implant can be retractable until a desired position is achieved.

Figure 1A:
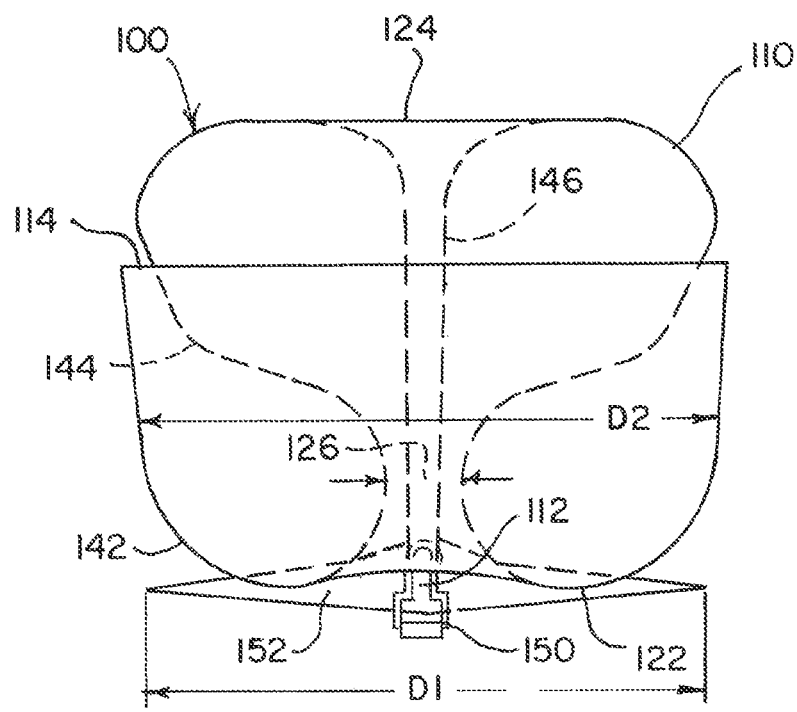
FIG. 1A is an illustration of an example implant having a tubular braid in a predetermined shape according to aspects of the present invention.
Figure 1B:
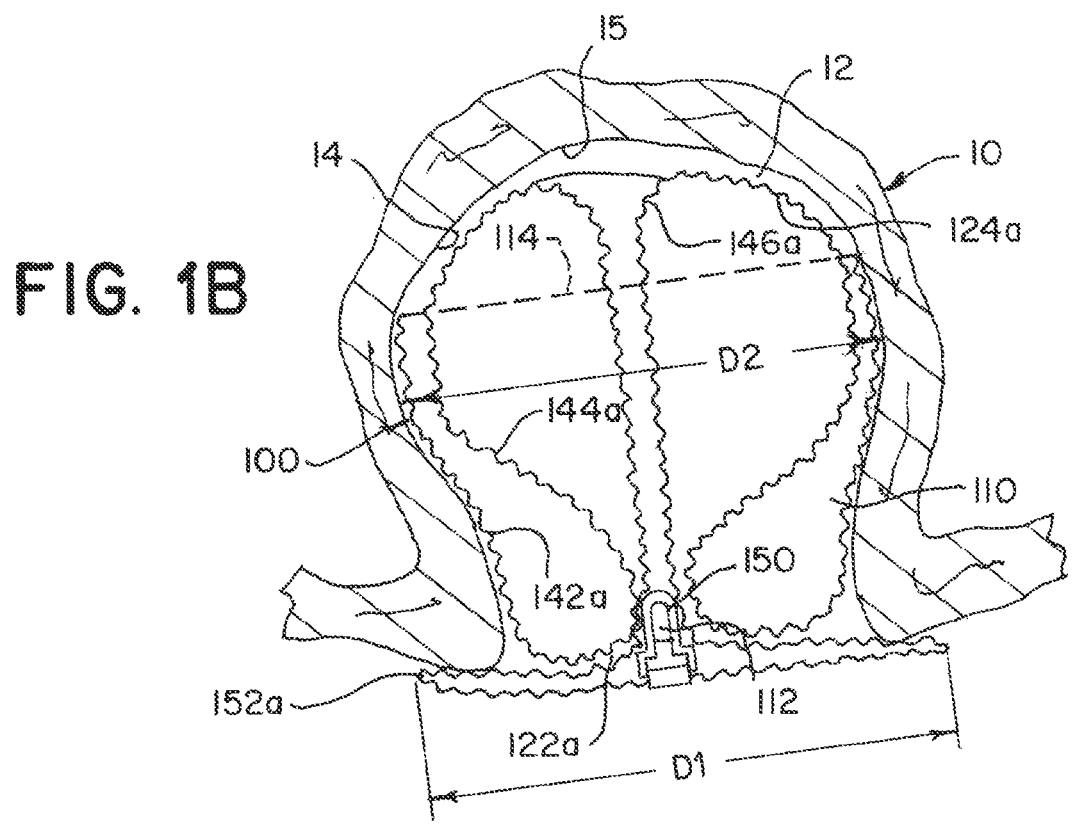
FIG. 1B is an illustration of the example implant with the tubular braid in a first implanted shape according to aspects of the present invention.

FIGS. 1A and 1B are illustrations of an example braided implant 100 that can have a predetermined shape as shown in FIG. 1A and a distinct implanted shape as illustrated in FIG. 1B. The implant 100 can treat a range of aneurysm sizes. The implant 100 can include a tubular braid 110 having an open end 114 and a pinched end 112. The implant 100 can include a connection and detachment feature 150 (referred to equivalently as "connection feature" and "detachment feature" herein) attached to the braid 110 at the pinched end 112. The pinched end 112 can include a marker band and/or soldered point with visibility, and/or the connection feature 150 can include radiopaque material. The tubular braid 110 can be formed in the predetermined shape (FIG. 1A), collapsed for delivery through a microcatheter, attached to a delivery system at connection feature 150, and implanted in an implanted shape such as the one shown in FIG. 1B.

Referring to FIG. 1A, when in the predetermined shape, the tubular braid 110 can include two inversions 122, 124, a pinched end 112, and an open end 114. The tubular braid 110 can include four segments, 142, 144, 146, and 152. The first segment 142 can extend from the open end 114 of the tubular braid 110 to a proximal inversion 122. The second segment 144 can be encircled by the open end 114 and extend from the proximal inversion 122 to a distal inversion 124. The third segment 146 can be surrounded by the second segment 144 and extend from the distal inversion 124 to the proximal inversion 122. The first segment 142, second segment 144, and third segment 146 can form the first portion of the tubular braid 110. The fourth segment 152 can extend from the third segment 146 radially outward from a central axis to cross the proximal inversion 122, fold, and converge at the pinched end 112. The fourth segment 152 can be partially encircled by the proximal inversion 122.

When in the predetermined shape, the tubular braid 110 can be substantially radially symmetrical about a central vertical axis. The detachment feature 150 is illustrated in FIG. 1A as a flat key that can be used with a mechanical delivery implant system (not pictured). The tubular braid 110 can be formed into the predetermined shape by first inverting the braid outwardly to separate the third segment 146 from the second segment 144 with a distal inversion 124. Then, the second segment 144 can be shaped over a form to produce the substantially "S" shaped profile illustrated in FIG. 1A. Next, the braid 110 can be inverted outwardly again to separate the second segment 144 from the first segment 142 with a proximal inversion 122. Finally, the fourth segment 152 can be shaped by expanding the fourth segment 152 radially. The fourth segment 152 can be pressed distally into the first portion of the tubular braid 110. It can also be advantageous to minimize a neck opening 126 defined by the lower extension of the "S" shape of second segment 144 to maximize occlusion of an aneurysm neck when the implant 100 is implanted.

The tubular braid 110 can include memory shape material that can be heat set to a predetermined shape, can be deformed for delivery through a catheter, and can self-expand to an implanted shape that is based on the predetermined shape and confined by the anatomy of the aneurysm in which it is implanted. When the tubular braid 110 is in the predetermined shape as depicted in FIG. 1A, the fourth segment 152 can comprise a diameter D1 greater than or approximately equal to a maximum diameter D2 of the first segment 142. Alternatively, when the tubular braid 110 is in the predetermined shape as depicted in FIG. 1A, the fourth segment 152 can comprise a diameter D1 lesser than a maximum diameter D2 of the first segment 142. When the tubular braid 110 is in the predetermined shape (FIG. 1A), the second segment 144 can form a sack, and at least a portion of the third segment 146 can positioned within the sack and at least a portion of the fourth segment 152 can be positioned external to the sack. As illustrated (FIG. 1B), when implanted, the fourth segment 152 can be positioned external to the aneurysm sac, extending across the aneurysm neck 16. Preferably, the fourth segment 152 can appose vasculature walls surrounding the aneurysm neck 16 when implanted. Alternatively, the shaped fourth segment 152 can also be placed within the aneurysm sac. The detachment feature 150 can be implanted centrally in the aneurysm neck 16. The detachment feature 150 can be positioned external to the sac 12.

The tubular braid 110 in the implanted shape (FIG. 1B) can be radially or vertically compressed or extended compared to the predetermined shape. As illustrated in FIG. 1B, when in the implanted shape, the braid 110 can have an outer layer 142a corresponding to the first segment 142 of the predetermined shape and positioned to contact an aneurysm wall 14 of the aneurysm 10, a proximal inversion 122a corresponding to the proximal inversion 122 of the predetermined shape and positioned to be placed approximate a neck 16 of the aneurysm 10, and a sack 144a corresponding to the second segment 144 of the predetermined shape and positioned to appose a portion of the aneurysm wall 14 of the aneurysm 10 and apposing the outer layer 142a. A distal inversion 124a can correspond to the distal inversion 124 of the predetermined shape, a third segment 146a can correspond to the third segment 146 in the predetermined shape. The braid 110 can also have a fourth segment 152a corresponding to the fourth segment 152 of the predetermined shape and extending from the third segment 146a radially outward from a central axis to cross the proximal inversion 122a, fold, and converge at the pinched end 112. As described in FIG. 1A, the fourth segment 152a can be pressed distally into the first portion of the tubular braid 110.

By pressing the fourth segment 152a distally into the first portion of the tubular braid 110, the first portion 142a, 144a, 146a of the tubular braid 110 can be moved towards the distal portion of an aneurysm wall 15 to occlude a portion of the neck 16 of the aneurysm 10. Pushing the fourth segment 152a into the first portion of the braid 110 can help conform the implant 100 to the shape of the aneurysm 10 and resist compaction. The fourth segment 152a when expanded radially and pressed into the first portion of the braid 110 also can provide additional coverage at the neck 16 of the aneurysm 10 to increase thrombosis and seal the aneurysm 10. When the fourth segment 152a is pressed into the first portion of the braid 110, three layers of braid are present at the neck of the aneurysm. The fourth segment 152a can cover spatial gaps between the first portion of implanted tubular braid 110 and the aneurysm neck 16, and can potentially increase metal coverage, decrease porosity of the implant 100, and increase stasis and blood flow diversion at the neck 16 of the aneurysm 10 to promote the sealing and thrombosis of the aneurysm 10. The fourth segment 152a can be shaped to occlude the majority of an aneurysm neck 16 when the device 100 is implanted. The fourth segment 152a can be shaped to completely occlude an aneurysm neck 16 when the device 100 is implanted.

When the tubular braid 110 is in the implanted shape (FIG. 1B), the fourth segment 152a can comprise a diameter D1 greater than or approximately equal to a maximum diameter D2 of the first segment 142a. Alternatively, when the tubular braid 110 is in the implanted shape (FIG. 1B), the fourth segment 152a can comprise a diameter D1 lesser than a maximum diameter D2 of the first segment 142a. When the tubular braid 110 is in the implanted shape (FIG. 1B), the second segment 144a can form a sack, and at least a portion of the third segment 146a can be positioned within the sack and at least a portion of the fourth segment 152a can be positioned external to the sack. The shaped fourth segment 152a can also be placed within the aneurysm sac 12 with only the detachment point 150 external to the sac 12.

Figure 2A:
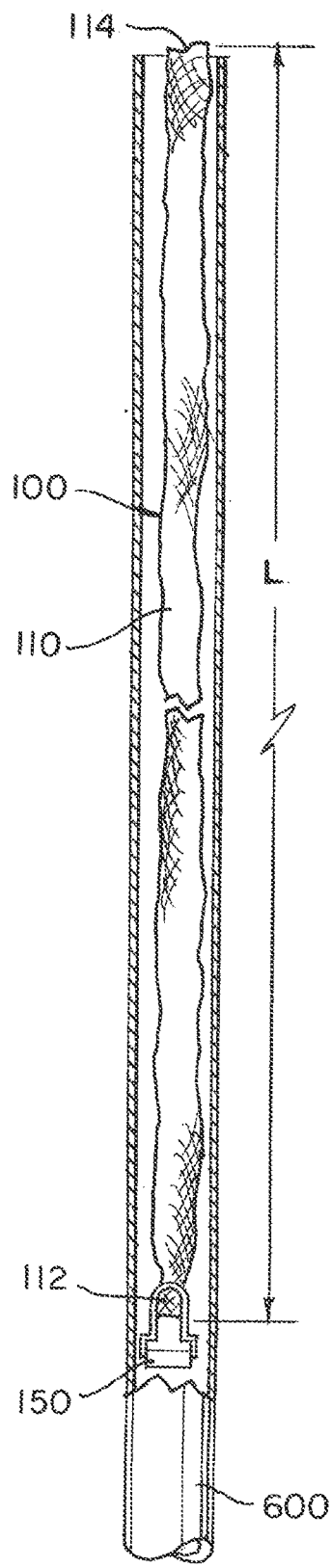

FIGS. 2A through 2I are illustrations of an example implant 100 having a braid 110 expanding to an implanted shape that is based on a predetermined shape and the anatomy of the aneurysm and nearby blood vessel as the braid 110 exits a microcatheter 600. The implant 100 has a predetermined shape similar to the shape illustrated in FIG. 1A. As illustrated in FIG. 2A, the braid 110 can be shaped to a delivery shape that is extended to a single layer of tubular braid having a compressed circumference/diameter sized to be delivered through the microcatheter 600 and a length L. As will be appreciated and understood by a person of ordinary skill in the art, the length L of a specific braid 110 can be tailored based on the size and shape of the aneurysm being treated. The length L can be approximately 1 inch in length.

Figure 2B:
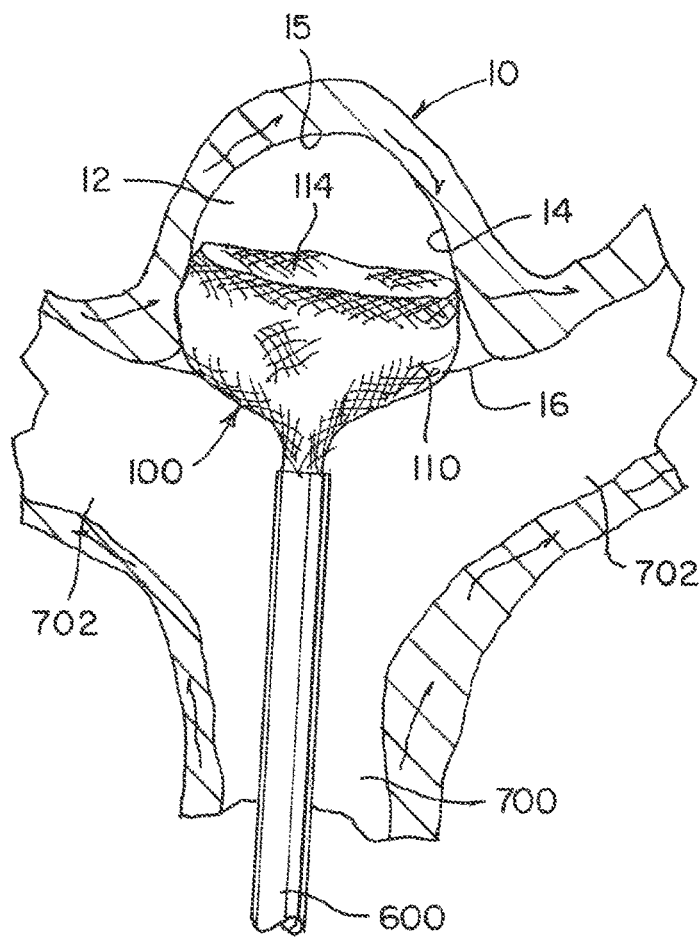
Figure 21:
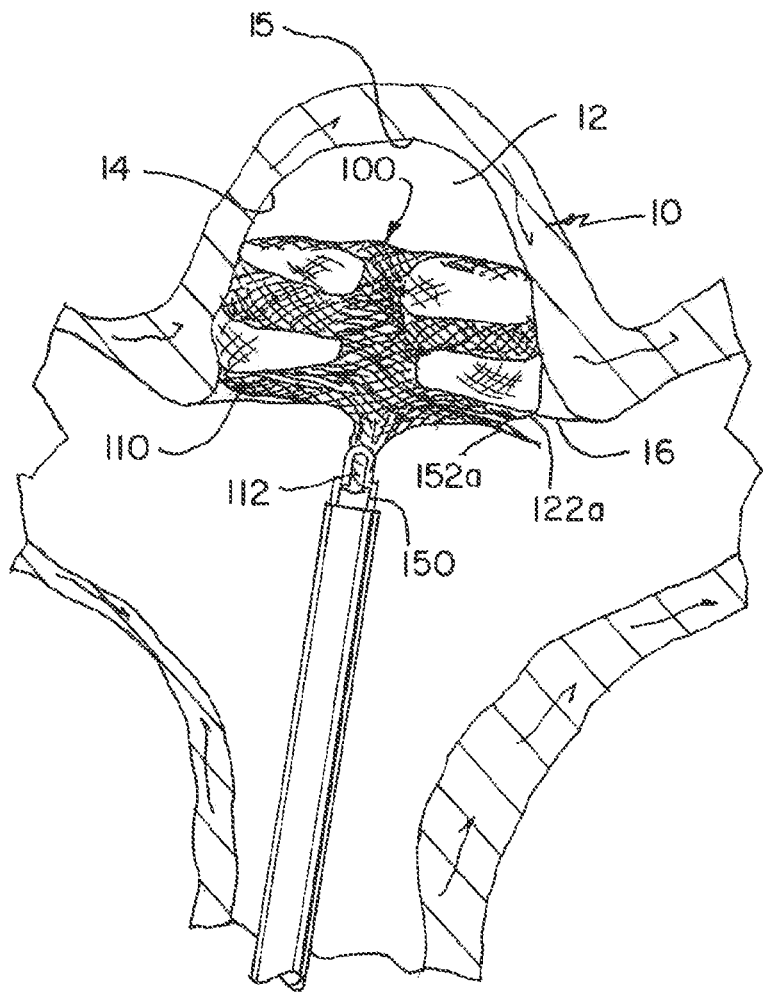

During delivery through the microcatheter 600, the detachment feature 150 can be attached to a delivery system at a proximal end of the implant 100, the pinched end 112 can be positioned near the proximal end of the implant 100, and the open end 114 can define the distal end of the implant 100. Collapsing the braid 110 to a single layer tube can result in a braid 110 that has a sufficiently small diameter and a sufficiently short length L to mitigate effects of friction force on the braid 110 when it is delivered through the microcatheter, allowing the braid 110 to be delivered unsheathed in some applications As illustrated in FIG. 2B, the implant 100 can be delivered to an aneurysm 10 through the microcatheter 600. The open end 114 can be positioned to exit the microcatheter 600 before any other portion of the braid 110 exits the microcatheter. The open end 114 can expand within the aneurysm sac 12 as it exits the microcatheter 600. The illustrated aneurysm 10 is positioned at a bifurcation including a stem blood vessel 700 and two branch vessels 702, and the microcatheter 600 is illustrated being delivered through the stem blood vessel 700. It is contemplated that the implant could be delivered to an aneurysm on a sidewall of a blood vessel through a curved microcatheter, and such a procedure is intended to be embraced by the scope of the present disclosure. As illustrated in FIG. 2C, the distal portion of the braid 110 can continue to expand radially within the aneurysm sac 12 as it exits the microcatheter 600. As the braid 110 is further pushed distally from the microcatheter 600, the braid 110 can appose the aneurysm wall 14 and conform approximate the aneurysm neck 16. The aneurysm 10 being treated can have a diameter that is less than the outer diameter of the tubular braid 110 in the predetermined shape so that the braid 110 tends to expand outwardly, providing a force against the aneurysm wall 14 and sealing approximate the perimeter of the aneurysm neck 16.

As illustrated in FIG. 2D, the braid 110 can form the proximal inversion 122a defining the first segment 142a as the braid 110 is further pushed out of the microcatheter 600. The proximal inversion 122a can be positioned approximate the aneurysm neck 16. The distal inversion 124a defining the second segment 144a can also begin to form as the braid 110 is pushed out of the microcatheter 600. As illustrated in FIGS. 2E through 2F, the "S" shape of the second segment 144a can begin to form as the braid 110 is further pushed from the microcatheter 600.

As illustrated in FIG. 2G, once the first portion of the braid 110, which can comprise the first segment 142a, second segment 144a, and third segment 146a, is in place within the aneurysm sac 12, the fourth segment 152a can radially expand outside the aneurysm 10 as the distal portion of the braid 110 continues to exit the microcatheter 600.

As illustrated in FIG. 2H, the fourth segment 152a can then be compressed distally as it continues to radially expand, compressing the fourth segment 152a up into the first portion of the braid 110.

Finally, as illustrated in FIG. 2I, the fourth segment 152a can be compressed distally into the first portion of the braid 110, at least partially occluding the neck 16 of the aneurysm 10 and the neck opening 126. The pinched end 112 and/or the detachment point 150 can remain external to the aneurysm sac once the fourth segment 152a has reached its final expanded and compressed state. The fourth segment 152a when compressed can be compressed to a minimal thickness as to not become an obstruction to the surrounding blood vessels.

Before the implant 100 is released from the delivery system, the implant 100 can be partially or fully retracted into the microcatheter 600 and repositioned.

Figure 3A:
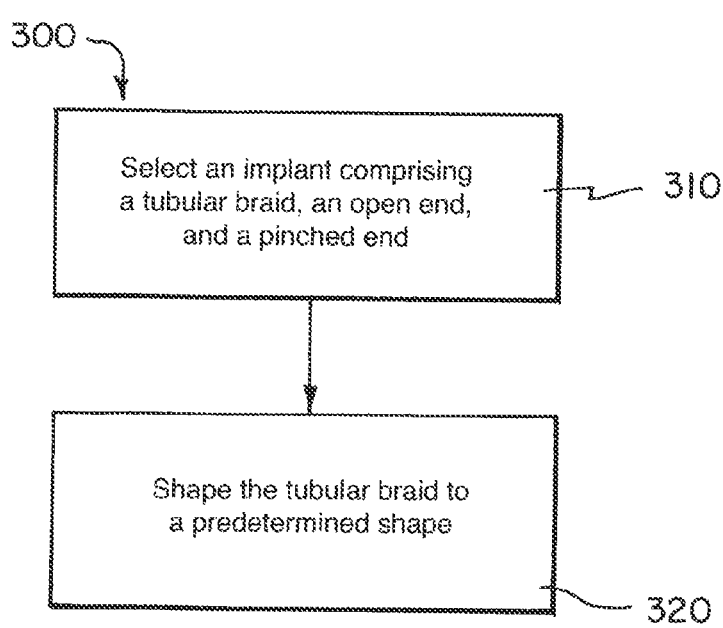

FIG. 3A is a flow diagram for a method 300 for forming an occlusive device to treat an aneurysm 10. Step 310 includes selecting an implant comprising a tubular braid, an open end, and a pinched end. Step 320 includes shaping the tubular braid to a predetermined shape, such as the one illustrated in FIG. 1A. As illustrated in FIG. 3B, step 320 can further comprise additional steps. Step 322 includes inverting the tubular braid to form a distal inversion. Step 324 inverts the tubular braid to form a proximal inversion by moving the open end over at least a portion of the braid. Step 326 includes shaping a first segment of the tubular braid extending between the open end and the proximal inversion. Step 328 shapes a second segment of the tubular braid extending between the proximal inversion and the distal inversion. Step 330 includes positioning the open end to encircle the second segment. Step 332 shapes a third segment extending from the distal inversion to the proximal inversion. Step 334 includes positioning the second segment to surround the third segment. Step 336 shapes a fourth segment of the tubular braid extending from the third segment radially outward from a central axis to cross the proximal inversion, fold inwardly toward the central axis, and converge at the pinched end. Step 338 includes positioning the fourth segment approximate a neck of an aneurysm.

In method 300, step 320 of shaping the tubular braid to the predetermined shape can further include shaping the fourth segment to comprise a diameter greater than or approximately equal to a maximum diameter of the first segment. In method 300, the step 320 of shaping the tubular braid to the predetermined shape can further include shaping the fourth segment to a diameter lesser than a maximum diameter of the first segment. The method 300 can further include shaping the tubular braided implant to a delivery shape sized to traverse a lumen of a microcatheter.

Figure 4A:
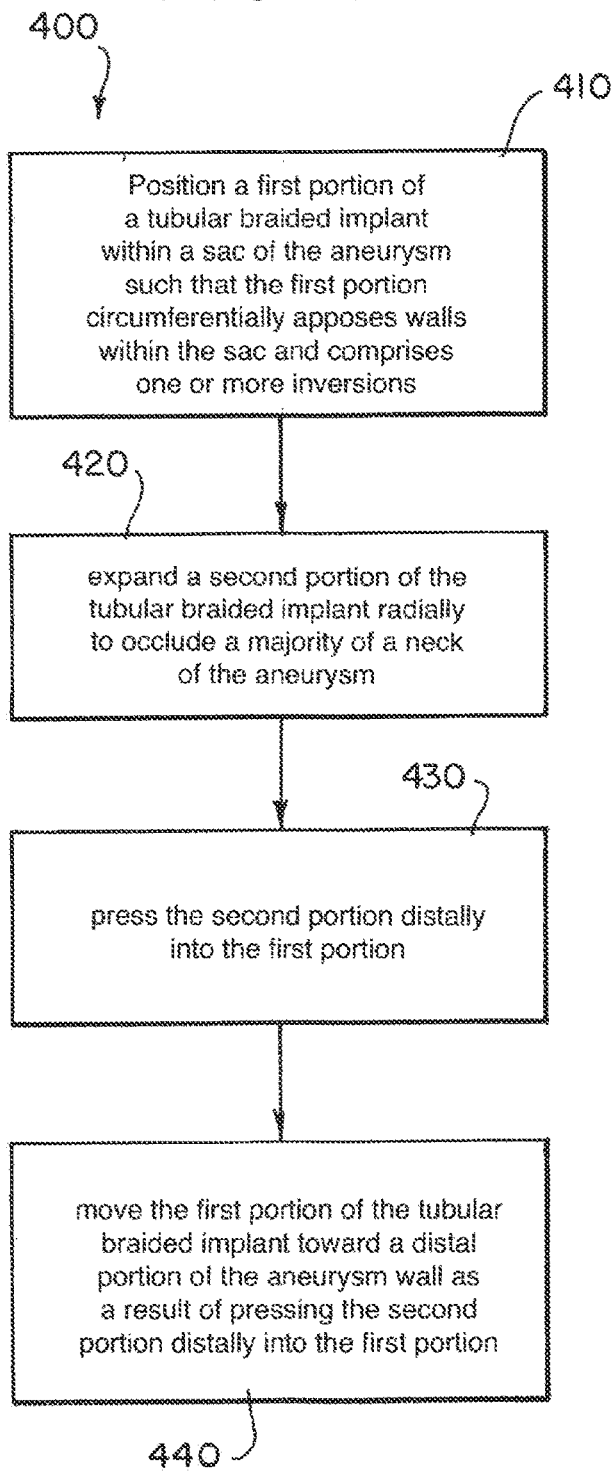
FIGS. 4A through 4B are flow diagrams for a method for treating an aneurysm.

FIG. 4A is a flow diagram for a method 400 for a method for treating an aneurysm 10. Step 410 positions a first portion of a tubular braided implant, the tubular braided implant comprising a tubular braid, an open end, and a pinched end, within a sac of the aneurysm such that the first portion circumferentially apposes walls within the sac. The first portion can include one or more inversions. Step 420 includes expanding a second portion of the tubular braided implant radially to occlude a majority of a neck of the aneurysm. Step 430 presses the second portion distally into the first portion. Pressing the second portion distally into the first portion can create three layers of braid at the neck of the aneurysm. The second portion can cover any spatial gaps between the first portion and the aneurysm neck, and can potentially increase metal coverage, decrease porosity of the implant, and increase stasis and blood flow diversion at the neck of the aneurysm to promote the sealing and healing of the aneurysm. Step 440 includes moving the first portion of the tubular braided implant toward a distal portion of the aneurysm wall as a result of pressing the second portion distally into the first portion.

Figure 4B:
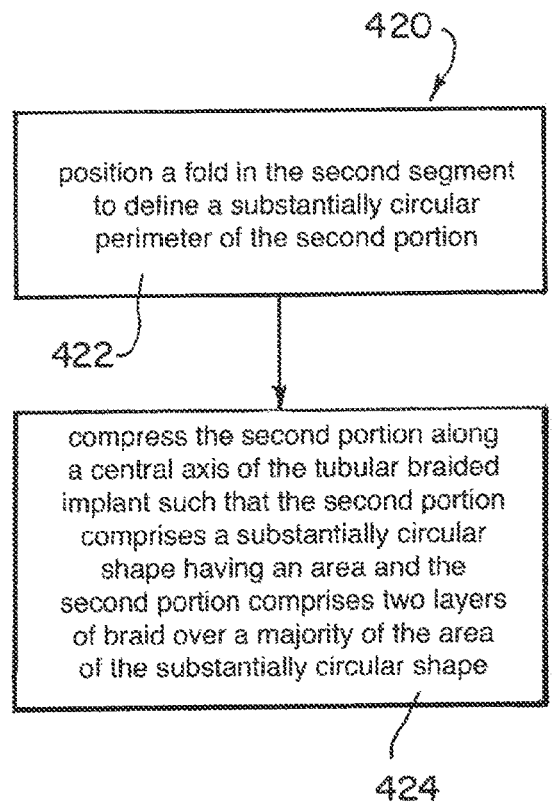

As illustrated in FIG. 4B, step 420 can further include step 422, which includes positioning a fold in the second segment to define a substantially circular perimeter of the second portion. Step 420 can additionally, or alternatively include step 424, which includes compressing the second portion along a central axis of the tubular braided implant such that the second portion comprises a substantially circular shape having an area and the second portion comprises two layers of braid over a majority of the area of the substantially circular shape.

Step 410 can further include shaping the tubular braided implant to form a columnar post encircling a central axis of the tubular braided implant and extending a majority of a height of the first portion. Step 410 can further include positioning a proximal inversion in the first portion of the tubular braided implant approximate the neck of an aneurysm and positioning a distal inversion in the first portion of the tubular braided implant approximate the distal portion of the aneurysm wall. Step 410 can further include positioning the open end of the tubular braided implant to circumferentially appose the aneurysm wall, shaping a first segment of the tubular braid extending between the open end and the proximal inversion to appose an at least a portion of a wall of the aneurysm within the aneurysm's sac, and shaping a second segment of the tubular braid such that the first segment provides an outwardly radial force in a plane defining a boundary between the aneurysm and blood vessel branches, the force sufficient to appose the first segment to walls of the aneurysm.

Step 430 can further include pressing the second portion of the tubular braided implant against the proximal inversion in the first portion of the tubular braided implant. Step 440 can further include moving the distal inversion in the first portion of the tubular braided implant toward the distal portion of the aneurysm wall.

The method 400 can further include shaping the tubular braided implant to form a columnar post encircling a central axis of the tubular braided implant and extending a majority of a height of the first portion. The method 400 can further include retracting the tubular braid until a desired position is achieved relative to the aneurysm. The method 400 can further comprise shaping the tubular braided implant to a delivery shape sized to traverse a lumen of a microcatheter.

As used herein, the terms "about" or "approximately" for any numerical values or ranges indicate a suitable dimensional tolerance that allows the part or collection of components to function for its intended purpose as described herein.

The descriptions contained herein are examples of embodiments of the invention and are not intended in any way to limit the scope of the invention. The invention contemplates many variations and modifications of the implant, including: alternative delivery methods, alternative braid materials, alternative means for achieving a desired stiffness/flexibility of braid material, additional structures affixed to the implant (e.g. to aid in anchoring the implant, blood flow diversion, embolism formation, etc.), alternative predetermined braid shapes (e.g. one inversion, three inversions, four inversions, five or more inversions, non-radially symmetric shapes, alternative segment shapes, etc.), alternative implanted shapes, etc. The invention contemplates many variations and modifications to constructing the implant to include combinations of the aforementioned variations and modifications of the implant. The invention contemplates many variations and modifications of implanting the implant to accommodate combinations of the aforementioned variations and modifications of the implant. Modifications apparent to one of ordinary skill in the art following the teachings of this disclosure are intended to be within the scope of the claims which follow.

What is claimed is:

1. An implant comprising:
    a tubular braid comprising an open end and a pinched end, the tubular braid further comprising a predetermined shape in which the tubular braid comprises:
    a first segment extending from the open end to a proximal inversion,
    a second segment encircled by the open end and extending from the proximal inversion to a distal inversion,
    a third segment surrounded by the second segment and extending from the distal inversion to the proximal inversion, and
    a fourth segment partially encircled by the proximal inversion and extending from the third segment radially outward from a central axis to cross the proximal inversion, fold, and converge at the pinched end.

2. The implant of claim 1,
    wherein, when the tubular braid is in the predetermined shape, the fourth segment comprises a diameter greater than or approximately equal to a maximum diameter of the first segment.

3. The implant of claim 1,
    wherein, when the tubular braid is in the predetermined shape, the fourth segment comprises a diameter lesser than a maximum diameter of the first segment.

4. The implant of claim 1,
    wherein, when the tubular braid is implanted in an aneurysm, the fourth segment occludes at least a portion of an aneurysm neck.

5. The implant of claim 1,
    wherein, when the tubular braid is in the predetermined shape, the second segment forms a sack, at least a portion of the third segment is positioned within the sack, and at least a portion of the fourth segment is positioned external to the sack.

6. The implant of claim 1, the tubular braid further comprising an implanted shape constrained by an aneurysm, in which the tubular braid comprises:
    an outer layer corresponding to the first segment of the predetermined shape and positioned to contact an aneurysm wall of the aneurysm,
    a proximal inversion corresponding to the proximal inversion of the predetermined shape and positioned to be placed approximate an aneurysm neck of the aneurysm, and
    a sack corresponding to the second segment of the predetermined shape and positioned to appose a portion of the aneurysm wall of the aneurysm and apposing the outer layer.

7. The implant of claim 6,
    wherein, when the tubular braid is in the implanted shape, the fourth segment comprises a diameter greater than or approximately equal to a maximum diameter of the first segment.

8. The implant of claim 6,
wherein, when the tubular braid is in the implanted shape, the fourth segment comprises a diameter lesser than a maximum diameter of the first segment.

9. The implant of claim 6,
wherein, when the tubular braid is in the implanted shape, the fourth segment occludes at least a portion of an aneurysm neck.

\* \* \* \* \*